(12) United States Patent
Muller et al.

(10) Patent No.: US 9,052,285 B2
(45) Date of Patent: Jun. 9, 2015

(54) METHOD FOR DETERMINING THE PH VALUE OF A LIQUID AND SENSOR ARRANGEMENT

(71) Applicant: EADS Deutschland GmbH, Ottobrunn (DE)

(72) Inventors: Gerhard Muller, Grafing (DE); Andreas Helwig, Munich (DE); Alois Friedberger, Oberpframm (DE); Angelika Hackner, Munich (DE)

(73) Assignee: EADS DEUTSCHLAND GmbH, Ottobrunn (DE)

( * ) Notice: Subject to any disclaimer, the term of this patent is extended or adjusted under 35 U.S.C. 154(b) by 50 days.

(21) Appl. No.: 13/747,108

(22) Filed: Jan. 22, 2013

(65) Prior Publication Data
US 2013/0188171 A1    Jul. 25, 2013

(30) Foreign Application Priority Data
Jan. 23, 2012 (DE) .......................... 10 2012 100 540

(51) Int. Cl.
| | | |
|---|---|---|
| G01N 21/00 | (2006.01) | |
| G01N 21/63 | (2006.01) | |
| G01N 21/33 | (2006.01) | |
| G01N 21/3577 | (2014.01) | |
| G01N 21/80 | (2006.01) | |

(52) U.S. Cl.
CPC ............... *G01N 21/63* (2013.01); *G01N 21/33* (2013.01); *G01N 21/3577* (2013.01); *G01N 2201/0625* (2013.01); *G01N 21/80* (2013.01)

(58) Field of Classification Search
USPC .......... 356/432–440, 244, 246; 436/163, 168, 436/131, 133; 422/82.05, 82.09, 400, 552
See application file for complete search history.

(56) References Cited

U.S. PATENT DOCUMENTS

| | | | |
|---|---|---|---|
| 4,945,171 A | | 7/1990 | Haugland et al. |
| 5,108,932 A | * | 4/1992 | Wolfbeis ........................ 436/124 |
| 5,567,624 A | | 10/1996 | Smith |
| 5,672,515 A | * | 9/1997 | Furlong ......................... 436/133 |
| 5,792,050 A | | 8/1998 | Alam et al. |
| 6,107,691 A | | 8/2000 | Gore et al. |
| 7,041,493 B2 | * | 5/2006 | Rao ............................ 435/288.1 |
| 7,842,507 B1 | | 11/2010 | Byrne |

(Continued)

FOREIGN PATENT DOCUMENTS

| | | |
|---|---|---|
| DE | 10 2005 051583 A1 | 5/2007 |
| WO | 2009/150325 A1 | 12/2009 |

OTHER PUBLICATIONS

Extended European Search Report of the corresponding European Patent Application No. EP 13 15 1976.1, dated on May 3, 2013.

(Continued)

*Primary Examiner* — Hoa Pham
(74) *Attorney, Agent, or Firm* — Global IP Counselors, LLP

(57) ABSTRACT

A system and method for determining the pH value of a liquid. The system and method excite the liquid molecules in the liquid by light with a predetermined wavelength and an intensity component, transmitted through the liquid in a predetermined wavelength range, of the light used for excitation is captured. This intensity component is used to produce a wavelength/intensity absorption characteristic and this absorption characteristic is related to a reference absorption characteristic associated with a specific pH value of the liquid. The system and method thus can be used to obtain drinking water from a fuel for aircraft.

20 Claims, 9 Drawing Sheets

(56) References Cited

U.S. PATENT DOCUMENTS

| | | | |
|---|---|---|---|
| 2004/0181131 A1 | 9/2004 | Maynard et al. | |
| 2008/0285011 A1 | 11/2008 | Shakespeare et al. | |
| 2009/0177143 A1* | 7/2009 | Markle et al. | 604/66 |
| 2010/0196918 A1* | 8/2010 | Ellis et al. | 435/7.1 |

OTHER PUBLICATIONS

James L. Weishaar et al., "Evaluation of Specific Ultraviolet Absorbance as an Indicator of the Chemical Composition and Reactivity of Dissolved Organic Carbon", Environmental Science and Technology, vol. 37, No. 20, 2003, p. 4702-4708, Oct. 1, 2003.

Todd R. Martz et al., "A Submersible Autonomous Sensor for Spectrophotometric pH Measurements of Natural Waters", American Chemical Security, Department of Chemistry, The University of Montana, Missoula, Montana 59812, Analytical Chemistry, vol. 75, No. 8, p. 1844-1850, Apr. 15, 2003.

German Office Action of corresponding German Patent Application No. 10 2012 100 540.0, dated on Aug. 22, 2012.

* cited by examiner

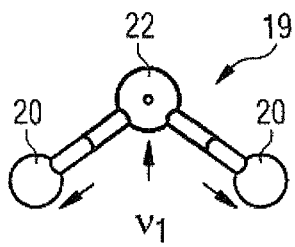
FIG 2A
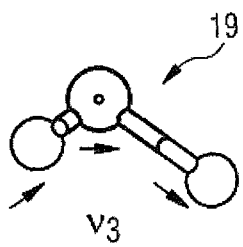
FIG 2B
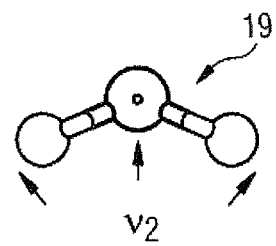
FIG 2C
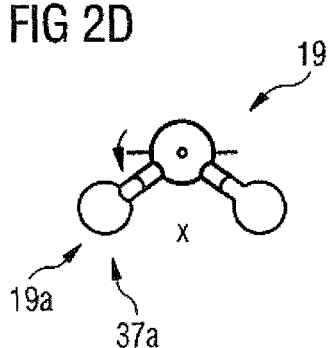
FIG 2D
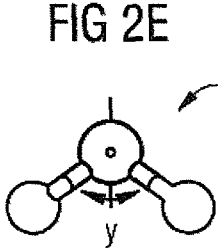
FIG 2E
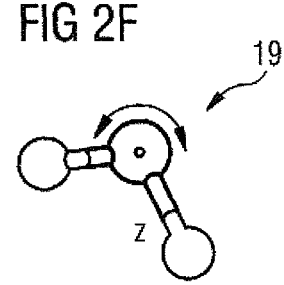
FIG 2F
FIG 3
| Gas | $\nu_1$, cm-1 | $\nu_2$, cm-1 | $\nu_3$, cm-1 |
| --- | --- | --- | --- |
| $H_2^{16}O$ | 3657.05 | 1594.75 | 3755.93 |
| $H_2^{17}O$ | 3653.15 | 1591.32 | 3748.32 |
| $H_2^{18}O$ | 3649.69 | 1588.26 | 3741.57 |
| $HD^{16}O$ | 2723.68 | 1403.48 | 3707.47 |
| $D_2^{16}O$ | 2669.40 | 1178.38 | 2787.92 |
| $T_2^{16}O$ | 2233.9 | 995.37 | 2366.61 |

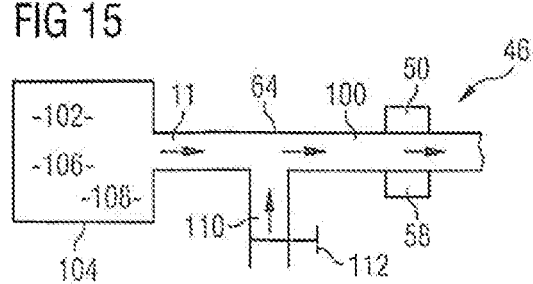
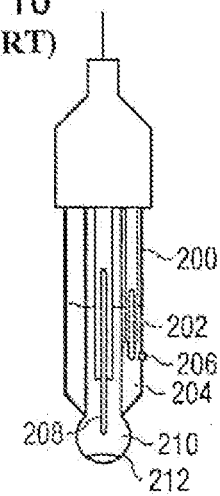
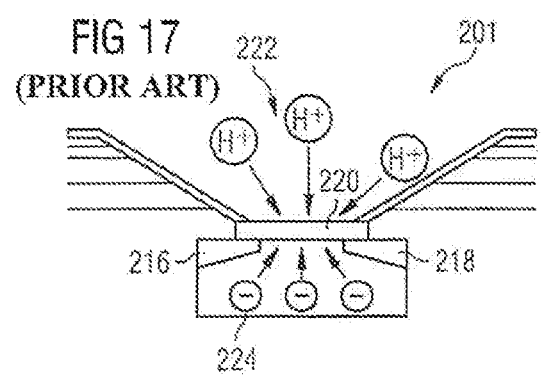

METHOD FOR DETERMINING THE PH VALUE OF A LIQUID AND SENSOR ARRANGEMENT

CROSS-REFERENCE TO RELATED APPLICATIONS

This application claims priority under 35 U.S.C. §119(a) to German Patent Application No. 10 2012 100 540.0, filed in Germany on Jan. 23, 2012, the entire contents of German Patent Application No. 10 2012 100 540.0 are hereby incorporated herein by reference.

BACKGROUND

1. Field of the Invention

The present invention relates to a method for determining the pH value of a liquid, a method for monitoring the pH value of a liquid, a method for obtaining drinking water from a fuel for aircraft and a sensor arrangement for determining the pH value of a liquid.

2. Background Information

In addition to electric power, fuel cells that are operated with kerosene also produce deoxygenated air and water. The water produced thus must be mineralized in order to purify the water to make drinking water. The mineralization process can be monitored using a pH sensor, which, by way of the pH value of the water, determines whether the mineralization of the water from the fuel cell is already sufficient for the water to have drinking-water quality.

The pH value is usually measured by means of ion-selective electrodes such as e.g. a glass electrode 200, shown in FIG. 16, or by means of ion-sensitive field effect transistors 201, as shown in FIG. 17. If a glass electrode 200 as shown in FIG. 16 is used, a reference electrode 202, which is usually immersed in a 0.1 molar KCl solution 204, is in electric contact via a diaphragm 206 to a measurement solution, the pH value of which is to be determined. Here, although the diaphragm 206 enables the electric contact with the measurement solution, it prevents mass transfer between the measurement solution and the KCl solution 204 to the greatest possible extent.

Arranged in the interior of the glass electrode 200 there is a measurement electrode 208, which is usually immersed into a phosphate buffer solution set to pH=7 as inner solution 210. The measurement electrode 208 has a conductive connection to the measurement solution via a very thin glass membrane 212. There are freely mobile sodium and lithium ions in the glass membrane 212; the glass membrane 212 is impermeable to hydrogen ions.

Upon contact with the aqueous solution, the glass membrane 212 starts to swell on the surface and hydrogen ions can take up lattice sites on oxygen anions of the glass membrane 212. In the case of a low pH value, this pushes the sodium and lithium ions back into the membrane, and so a modified potential can be measured at the measurement electrode 208. By contrast, in the case of a high pH value, a potential with opposite sign is created because the process runs in the other direction.

As an alternative to the glass electrode 200, use can be made of an ion-sensitive field effect transistor 201, which, as a simple transistor, is provided with a voltage source 216 and a voltage drain 218, which are separated from one another by an insulator 220. Hydrogen ions 222 from the measurement solution, the pH value of which is to be measured, are deposited on the insulator 220, which is usually formed by an oxide lattice. In the process, a positive voltage is created on the outer side of the insulator 220, which is mirrored on the inner side of the insulator 220. This means that a negative voltage 224 is created there. The higher the pH value of the measurement solution is, i.e. the fewer $H^+$ ions are present in the measurement solution, the fewer hydrogen ions 222 are deposited on the insulator 220 and the negative voltage which flows between voltage source 216 and voltage drain 218 reduces. Conversely, the voltage increases between the voltage source 216 and the voltage drain 218 if there is a lower pH value, because more hydrogen ions 222 can be deposited on the insulator 220 in this case.

The two measurement methods, shown in FIGS. 16 and 17, for determining the pH value of a measurement solution are both disadvantageous in that they need to be immersed into the medium to be measured in order thereby to come into contact therewith. In doing so, there is a risk of dirtying the measurement solution and also the respective sensor. Furthermore, the sensors must be recalibrated at regular intervals in the case of electrochemical pH measurements in order to obtain reliable and reproducible measurement results in respect of the pH value.

SUMMARY

It is therefore an object of the invention to propose a method for determining the pH value of a liquid, which method overcomes the aforementioned disadvantages. This object is achieved by a method for determining the pH value of a liquid according to the enclosed embodiments. A method for monitoring the pH value of a liquid, a method for obtaining drinking water from a fuel for aircraft and a sensor arrangement for determining the pH value of a liquid can also be achieved by the disclosed embodiments.

For example, a method for determining the pH value of a liquid, in particular an aqueous solution, comprises exciting liquid molecules in the liquid using light with a predetermined wavelength, capturing an intensity component, transmitted by the liquid in a predetermined wavelength range, of the light used for excitation, producing a wavelength/intensity absorption characteristic from the captured intensity component, and relating the produced absorption characteristic to a reference absorption characteristic associated with a specific pH value of the liquid.

The method according to the invention is based on the discovery that liquids, in particular aqueous solutions, have different light-absorption characteristics depending on the pH value thereof. Hence, depending on pH value, a liquid irradiated by light transmits a different intensity component of the light in a predetermined wavelength range, and so it is possible to determine the actual pH value of the liquid by relating the measurement result to a previously known absorption characteristic of the liquid at a specific pH value.

The method can be carried out by optical devices and is advantageous in that there is no need to immerse probes into the liquid to be measured; the method can accordingly be carried out contactlessly. An additional advantage thereof is that drift effects as a result of a deterioration of the previously used probes due to corrosion or impurities no longer play a role. As a result, the method can be used to establish reliably the pH value of a liquid, in particular of an aqueous solution.

It is advantageously possible to convert into the optical absorption from the transmitted intensity component of the light used for excitation by means of the following equation:

$$T = (1-R) \times \exp(-\alpha \times d),$$

where T is the optical transmission, i.e., the transmitted intensity component of the light used for excitation, R is the reflection coefficient, d is the layer thickness of the measured liquid or of the utilized cuvette and a is the optical absorption.

Reference absorption characteristics can be produced by preferably making a concentration series of a plurality of solutions of the liquid to be measured, with the solutions having different known $H_3O^+$ concentrations. By way of example, this can be achieved by using different amounts of KOH and/or HCl. Then absorption spectra of these solutions are captured, with the respective absorption edge or the respective absorption peak lying at a different wavelength as a function of the pH value, which is known in the measured solution. If the absorption spectrum of the liquid whose pH value is to be determined is now advantageously compared to a series of reference absorption spectra, it is advantageously possible to determine the pH value of the measured liquid in a quick and simple fashion.

An absorption spectrum and/or a diffraction pattern are preferably produced. In an absorption spectrum, the absorbed intensity of the light used for excitation is plotted over a relatively large wavelength range, preferably as a function of the wavelength of the light used for excitation. In the process, absorption results in absorption edges and absorption peaks characteristic of each substance, depending on the observed wavelength range. It is then advantageously possible to directly deduce the pH value of the measured liquid from the precise position of the absorption edges or the absorption peaks, particularly if the pH characteristic position of the edge or of the peak is already known.

Alternatively and/or in addition thereto, it is also possible to produce a diffraction pattern, from which it is correspondingly possible to draw conclusions in respect of the pH value of the liquid.

Electronic transitions and/or vibrations are preferably excited in the liquid molecules. Here, electronic transitions result in characteristic absorption edges, the energetic position of which then advantageously allows conclusions to be drawn in respect of the pH value of the liquid. Alternatively, or else in addition thereto, it is possible to produce vibration absorption spectra by using light with a wavelength which excites vibrations in the liquid molecules, with it preferably being possible to deduce the pH value of the measured liquid from the position of characteristic vibration peaks. The liquid molecules are preferably excited by ultraviolet light, particularly by light in the wavelength range from 100 nm to 330 nm, more particularly in the wavelength range from 180 nm to 260 nm.

Ultraviolet light advantageously excites electronic transitions in the liquid molecules and absorption edges, i.e. energetic regions in which electrons are lifted to higher-energy levels in a molecular orbital, are preferably produced. These are discrete energy transitions, with the energy required for the transition depending on the split between an unoccupied and an occupied molecular orbital. This split in turn is dependent on the pH value of the liquid to be measured. Thus, depending on pH value, this advantageously results in a characteristic absorption edge when using UV light, which allows conclusions to be drawn in respect of the pH value of the measured liquid.

Alternatively, or in addition thereto, the liquid molecules are excited by light in the wavelength range of visible and/or mid infrared and/or near infrared light, particularly in the wavelength range from 800 nm to 1200 nm. In this lower-energy range, vibrations which lead to characteristic absorption peaks in the spectrum are preferably excited in the liquid molecules. In particular, O—H stretching vibrations are often excited in the wavelength range from 800 nm to 1200 nm, the exact energetic position of which stretching vibrations preferably depends on the strength of the absorbing O—H bond. In turn, the latter is advantageously dependent on the charge state of the central oxygen atom and hence also on the pH value of the liquid to be examined. As a result, it is advantageously possible, particularly when using light in the wavelength range from 800 nm to 1200 nm, to deduce the pH value of the examined liquid from the position of the vibration-absorption peaks.

It is preferable for a plurality of intensity components of the light used for excitation to be captured separately from one another in different predetermined wavelength ranges. An intensity pattern is particularly preferably produced as absorption characteristic from the plurality of separately captured intensity components.

By way of example, this can be realized by virtue of the fact that the transmitted intensity component of the light used for excitation is captured by different detectors, the latter preferably being optimized for capturing a specific wavelength by differently set band-pass filters.

This is advantageous because light of different wavelengths is absorbed to a different degree by liquids. Accordingly, there are different intensity losses on the detection side, depending on the observed wavelength. These intensity components, which are different depending on wavelength, are preferably captured separately from one another in order thus to achieve an advantageously particularly accurate measurement of the energetic position of the absorption of the liquid.

A characteristic intensity pattern is then particularly advantageously produced from a multiplicity of a plurality of separately captured intensity components, which intensity pattern is then compared to an intensity pattern of a solution with a known pH value in order thus, preferably, to determine the pH value of the measured liquid in a particularly precise fashion.

In a particularly preferred embodiment the liquid molecules are excited by pulsed light, in particular by A/C modulated light. This is how, in a particularly advantageous fashion, it is possible simultaneously to implement a self-test of the sensor arrangement because the pulse frequency of the emitted light output on the light source is preferably captured by the detector. If this is not the case, it can advantageously be deduced in a particularly simple fashion that there is a fault in the sensor arrangement.

The frequency of the intensity component of the pulsed light transmitted through the liquid is particularly preferably captured separately from one another in a plurality of different predetermined wavelength ranges. As a result, it is advantageously possible to check in an even more improved fashion whether the sensor arrangement is operating correctly because all utilized detectors preferably receive the pulsed light with the same frequency.

Advantageously, it is additionally possible also to capture the intensity of the light used for excitation, which is emitted by the light source, prior to entry into the liquid. Then it is preferably possible to normalize the intensity of the transmitted light, captured on the detector side, with respect to the actual output intensity of the light at the light source, and so effects which already occur at the light source can preferably be removed by calculation.

In a method for monitoring the pH value of a liquid, in particular an aqueous liquid, an above-described absorption characteristic of the liquid is created repeatedly and the spectral shift of the absorption characteristic between the individual captured absorption characteristics is captured. The absorption characteristics are advantageously produced at predetermined time intervals or continuously, in order thus, preferably, to obtain particularly reliable statements in respect of the pH value of the examined liquid.

In the process, samples are in particular taken from the liquid or the liquid is alternatively continuously conveyed past a corresponding sensor arrangement, such as a light source and/or a detector. Thus a chemically treated liquid can preferably be monitored continuously in respect of the pH value thereof during the chemical treatment.

In the case of a method for obtaining drinking water from a fuel for aircraft, the fuel in a fuel cell is initially electrolyzed to form water and further reaction products and mineral substances are then added to the produced water. The method for monitoring the pH value as described above is carried out concurrently with the addition of mineral substances, or alternatively at predetermined intervals, in order thus advantageously to be able to determine the point at which sufficient mineral substances have been added to the water in order to be able to declare the water to be drinking water.

A sensor arrangement for determining the pH value of a liquid, in particular an aqueous liquid, comprises a light source for irradiating the liquid with light exciting the liquid molecules of the liquid, a carrier apparatus for positioning the liquid in the beam path of the light used for excitation, a detector apparatus for capturing the intensity component, transmitted through the liquid, of the light used for excitation and a conversion apparatus for producing a wavelength/intensity absorption characteristic from the captured intensity component. Such a sensor arrangement can be used to determine the pH value of the liquid to be examined contactlessly and therefore it is possible to avoid impurities in the liquid or a deterioration of the sensor arrangement as a result of contamination and/or corrosion.

The light source is preferably formed by an LED, the emitted light of which in particular has an emission peak in the wavelength range from 255 nm to 270 nm and a spectral width of 40 nm to 60 nm. As a result, the LED advantageously emits light in the ultraviolet wavelength range and thus preferably excites electronic transitions in the liquid molecules. Thus, it is possible, for example, to produce an absorption spectrum in the range from 255 nm to 270 nm as absorption characteristic, with the absorption edge being characteristic of the pH value of the liquid. Alternatively, or in addition thereto, it is also possible to use LEDs which emit light in the wavelength range of visible (VIS), near infrared (NIR) or mid infrared (MIR) light.

The light source is particularly preferably configured to emit pulsed light, in particular A/C modulated light. Thus it is advantageously possible to implement a self-testing apparatus because the detector apparatus preferably captures the same pulse frequency as the light source emits. If this is not the case, it is advantageous that it can easily be seen that the sensor arrangement has a fault somewhere.

The carrier apparatus advantageously has a conveying apparatus for conveying the liquid past the light source and/or the detector apparatus. As a result, it is also advantageously possible for the liquid to be examined in respect of the pH value thereof while it is flowing past these.

The carrier apparatus particularly preferably has a region which is optically transparent to the light used for excitation, said region in particular being formed by sapphire or quartz windows. More preferably, provision is made for a temperature control apparatus for controlling the temperature of the liquid and, in addition or as an alternative thereto, for a temperature measuring apparatus for measuring the temperature of the liquid prior to irradiating the liquid by means of the light source. Since the pH value is also temperature dependent, it is advantageous if the temperature of the liquid to be measured is at least known. It is particularly advantageous if the liquid can be set to a predetermined temperature in order thus, preferably, to further simplify a comparison with known absorption characteristics.

The detector apparatus advantageously has at least one detector formed by a photodiode, which detector is preferably formed of Si, SiC, GaN or ZnO. Photodiodes formed from semiconductor materials are advantageous in that they are cost-effective and preferably only have low energy consumption.

In a particularly preferred embodiment, the detector apparatus has a detector array which comprises a plurality of detectors configured for separate capture of the intensity component of the light used for excitation in a plurality of different wavelength ranges. Since light with different wavelengths is absorbed to a different extent by a liquid, an arrangement of a plurality of detectors in a detector array results in a preferably improved and more precise measurement of the energy-dependent absorption of the liquid molecules.

The plurality of detectors are advantageously built such that they have photodiodes which are optimized for capturing different wavelengths using band-pass filters set to different wavelengths. The more precisely a detector is optimized to the wavelength that it should capture, the more precise the overall measurement advantageously also becomes. By way of example, it is possible to produce precise intensity patterns which preferably enable a particularly simple comparison with known intensity patterns.

In a particularly preferred embodiment, provision is made for a self-testing apparatus for testing the sensor arrangement in respect of functionality. Thus it is preferably possible to quickly capture whether performed measurements are relevant or not.

The self-testing apparatus advantageously has an overall monitoring apparatus for combined monitoring of all electronic and optical parts of the sensor arrangement. As a result, it is possible to capture—preferably quickly—whether one of the parts is not functioning correctly in order thus to quickly stop e.g. a chemical purification process.

In addition or as an alternative thereto, the self-testing apparatus has a light-source monitoring apparatus for monitoring the light intensity emitted by the light source. As a result, the light intensity captured by the detector and/or detectors can preferably be normalized with respect to the output light intensity of the light source such that shifts which already occur as a result of changes at the light source itself can preferably be removed by calculation.

The overall monitoring apparatus advantageously has a pulsed light source for emitting light which excites the liquid molecules, and a plurality of detectors for capturing separately from one another the pulse frequency of the light used for excitation in a plurality of different wavelength ranges. If light is emitted by the light source in pulsed fashion, all detectors preferably capture the same pulse frequency of the incident transmitted light if the electronic and/or optical parts of the sensor arrangement are functioning correctly. If this is not the case, it can preferably be deduced quickly that some part of the sensor arrangement is not functioning correctly.

The light-source monitoring apparatus advantageously has a beam splitter, arranged prior to the entry into the liquid in the beam path of the light used for excitation, for diverting a component of the light used for excitation, and a broad-band reference detector for capturing the intensity of the diverted light. Hence, part of the light emitted by the light source can—preferably in a simple fashion—already be fed into a reference detector prior to contact with the liquid, and so said reference detector can monitor the intensity of the emitted light, advantageously in a continuous fashion.

These and other objects, features, aspects and advantages of the present invention will become apparent to those skilled in the art from the following detailed description, which, taken in conjunction with the annexed drawings, discloses a preferred embodiment of the present invention.

BRIEF DESCRIPTION OF THE DRAWINGS

Referring now to the attached drawings which form a part of this original disclosure:

FIGS. 2A through 2F show various molecule-vibration types of the $H_2O$ molecule;

FIG. 3 shows absorption energies related to the vibrations shown in FIGS. 2A through 2F;

FIG. 15 shows how drinking water is obtained from kerosene;

FIG. 16 shows a glass electrode for measuring the pH value according to the prior art; and FIG. 17 shows an ion-sensitive field effect transistor for measuring the pH value of a liquid according to the prior art.

DETAILED DESCRIPTION OF EMBODIMENTS

Selected embodiments will now be explained with reference to the drawings. It will be apparent to those skilled in the art from this disclosure that the following descriptions of the disclosed embodiments are provided for illustration only and not for the purpose of limiting the invention as defined by the appended claims and their equivalents.

The concept of the invention is based on the discovery that the light absorption of a liquid 10 is pH-dependent. By way of example, this discovery is to be illustrated below on the basis of water 11 as a liquid 10.

Figure 1:
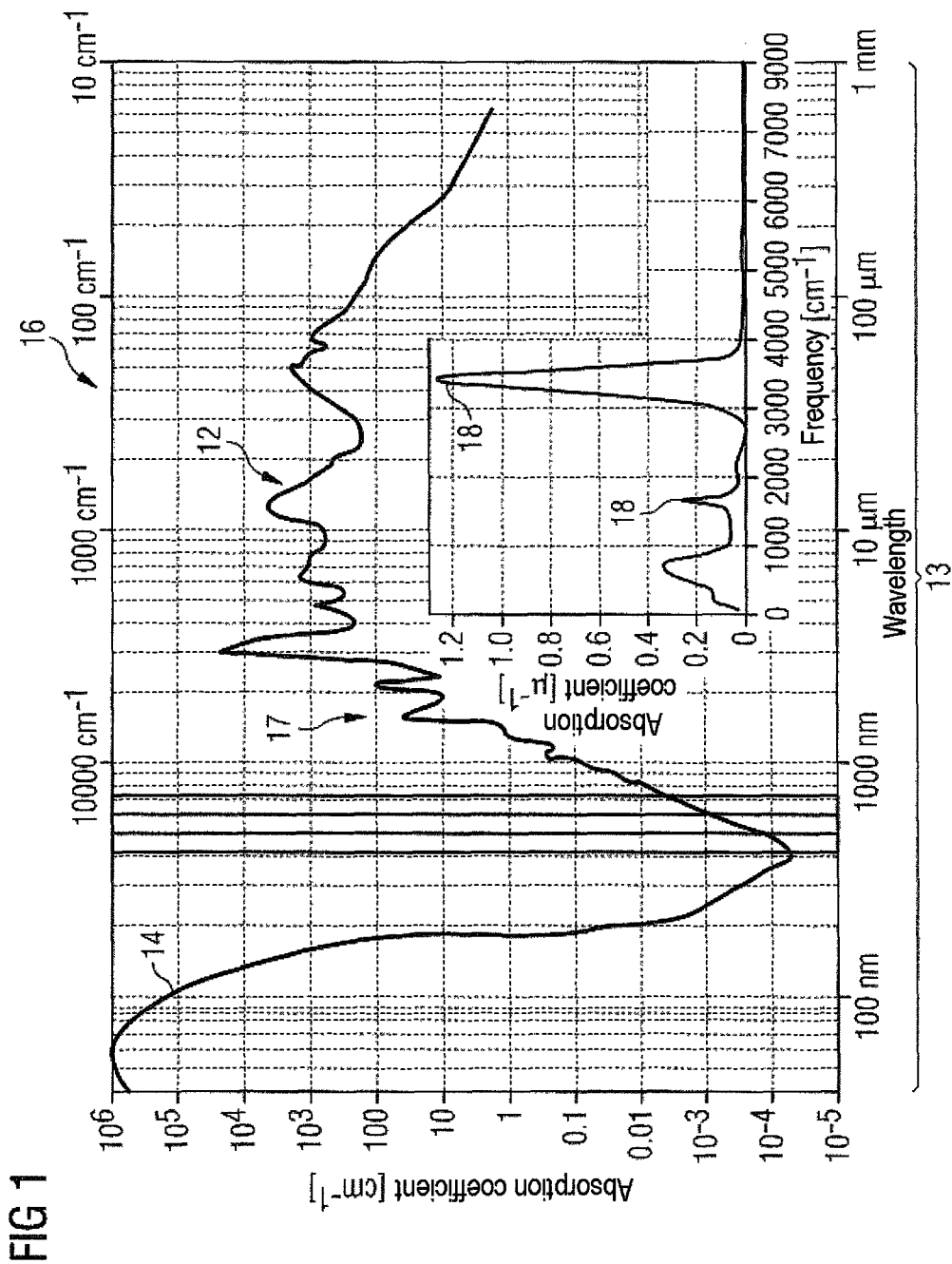
FIG. 1 shows a water absorption spectrum in the wavelength range between 40 nm and 1 mm.

FIG. 1 shows an absorption spectrum 12 in a wavelength range 13 between far ultraviolet light 13a and far infrared light 13a, said light being used for excitation. In the range between 100 nm and 300 nm the absorption spectrum 12 has a pronounced absorption edge 14 as absorption characteristic 16, i.e. only a specific intensity component 17 of the light 13a used for excitation is transmitted through the irradiated liquid 10 here. Absorption peaks 18 in the infrared range have been illustrated again as a magnified and normalized inlay in the absorption spectrum 12, but this time they are dependent on the wavenumber or frequency. It is possible to identify that water has characteristic absorption peaks 18 around 3600 $cm^{-1}$ and 1600 $cm^{-1}$ as a result of the vibration excitation.

The absorptions in the infrared range result from the excitation of vibration modes, i.e. of vibrations 19 of the water molecule 19a. Possible vibration forms are illustrated in FIGS. 2A through 2F. FIG. 2A shows a symmetric stretching vibration, in which hydrogen atoms 20 symmetrically move away from an oxygen atom 22 and toward it during the vibration 19. FIG. 2B shows an asymmetric stretching vibration, i.e. while one hydrogen atom 20 moves away from the oxygen atom 22, the other hydrogen atom 20 moves toward the oxygen atom 22. FIG. 2C shows a bending vibration, during which the bond angle of the oxygen-hydrogen bonds changes during the vibration 19. FIGS. 2D through 2F show librations about various axes.

FIG. 3 shows in tabular form the absorption frequencies associated with the vibrations 19 shown in FIGS. 2A through 2F for water molecules 19a with different weights. Three characteristic absorption peaks 18 $v_1$, $v_2$ and $v_3$ are listed for water with different compositions of the isotopes of hydrogen and oxygen. These absorption peaks 18 are reflected in the absorption spectrum 12 in the infrared range of FIG. 1.

Figure 4:
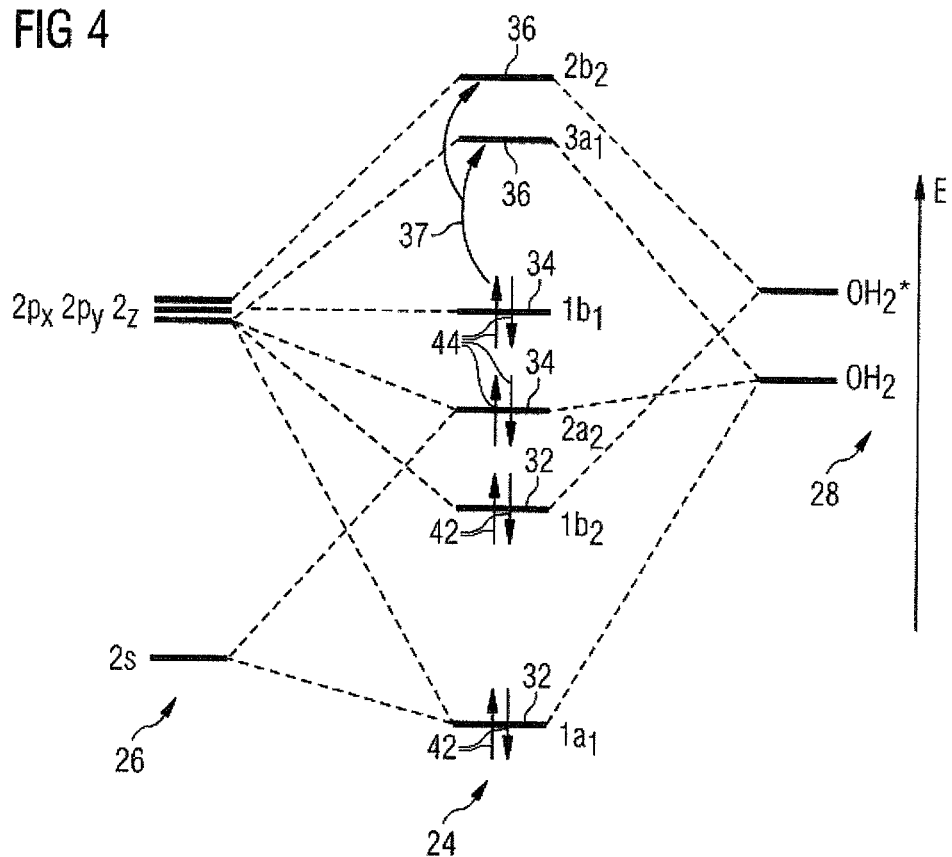
FIG. 4 shows the electronic structure of the $H_2O$ molecular orbital in energetic relation to the $O_2$ and $H_2$ atomic orbitals.

FIG. 4 shows the electronic structure or energetic position of the water molecular orbitals 24 in relation to the oxygen atomic orbitals 26 or the hydrogen molecular orbitals 28. The water molecular orbitals 24 denoted by $1a_1$ and $1b_2$ are bonding molecular orbitals 32, the water molecular orbitals 24 denoted by $2a_1$ and $1b_1$ are nonbonding molecular orbitals 34, and the water molecular orbitals 24 denoted by $3a_1$ and $2b_2$ are antibonding molecular orbitals 36.

Figure 5:
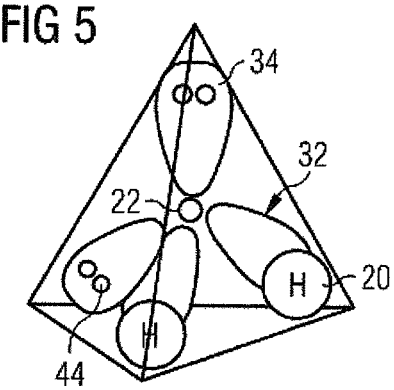
FIG. 5 shows the spatial arrangement of the atoms and free electron pairs in the $H_2O$ molecule.

FIG. 5 shows a spatial representation of the water molecule 19a and the bonding molecular orbitals 32 and the nonbonding molecular orbitals 34. In the case of excitation by light 13a having a suitable wavelength, it is possible, for example, for electrons to be excited from the nonbonding molecular orbital 34, denoted by $1b_1$ in FIG. 4, into one of the antibonding molecular orbitals 36. Energetic excitation of electrons leads to electronic transitions 37 in higher molecular orbitals and usually occurs in the ultraviolet range. The process is so fast that the excitation only has a negligible effect on the atomic spacing of the atoms present in the molecule; this is also known as Franck-Condon principle.

FIGS. 1 through 5 therefore illustrate, in graphical form, the theoretical principles for energetic excitation of liquid molecules 37a using the example of water 11 in the infrared range and in the ultraviolet range. FIGS. 6 through 9 show specific absorption spectra 12 and transmission spectra 38 of water 11 in the ultraviolet range.

Figure 6:
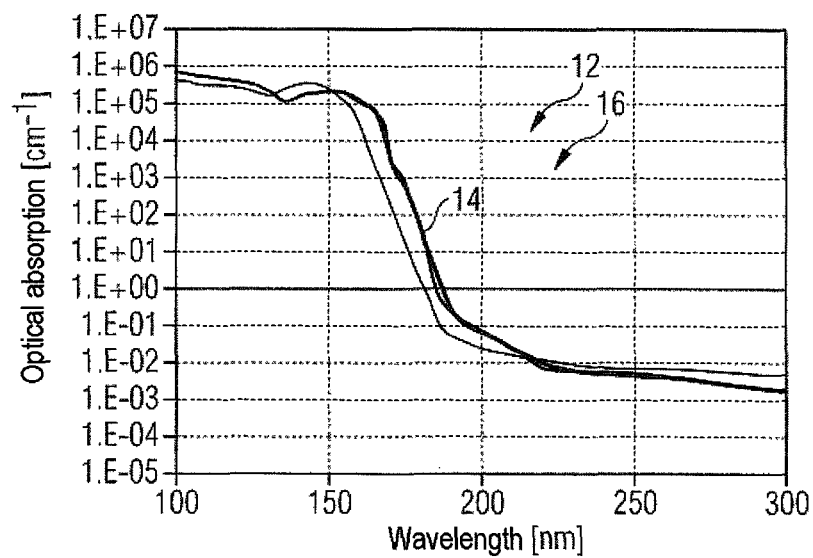
FIG. 6 shows a plurality of absorption edges of water in the ultraviolet range according to literature citations.

That is, FIG. 6 shows different spectra 40, found in the literature, of water 11 in the ultraviolet wavelength range 13 between 100 nm and 300 nm, in which the absorption edge 14 in the region around 175 nm can clearly be identified. As already mentioned above, the concept of the invention is based on the discovery that absorption spectra 12, or, in the specific case, the absorption edge 14 of the water 11 in the ultraviolet range, is pH-dependent. The deviation of the spectra 40, found in the literature, shown in FIG. 6 could be explained to be the result of these spectra 40, found in the literature, having inadvertently been measured at different pH values of the water 11.

Figure 7:
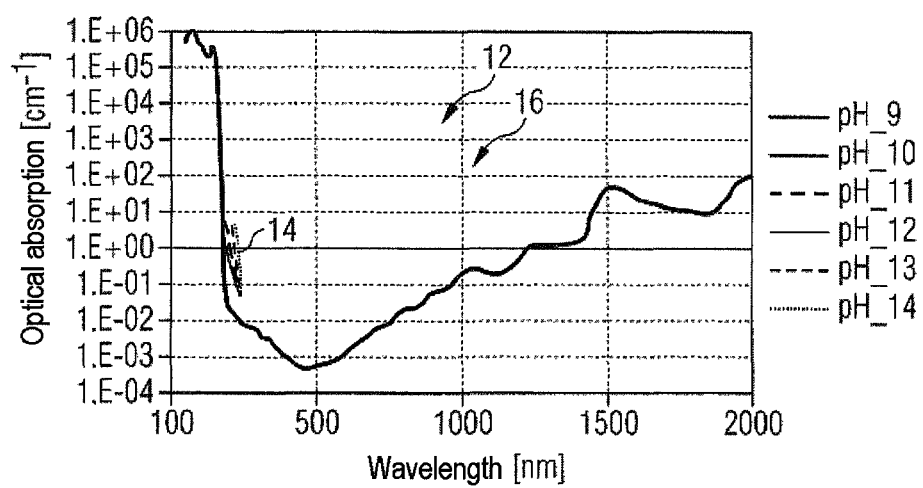
FIG. 7 shows an overview absorption spectrum in the ultraviolet range at different pH values of the measured liquid.

FIG. 7 shows an overview absorption spectrum 12 of water 11 at different pH values from pH=9 to pH=14 in the wavelength range 13 between 0 nm and 2000 nm. In order to make the effects more visible, the range between 100 nm and 300 nm has been illustrated in FIG. 8 in a magnified fashion. The complete spectrum between 100 nm and 300 nm is a spectrum 40 from the literature. The spectra between 180 nm and 250 nm are pH-dependent measured absorption spectra 12. It is possible to identify that the absorption edge 14 of the water at pH=14 has been bathochromically shifted furthest in the direction of lower energies. The lower the pH value of the respectively measured liquid 10, in this case water 11, becomes the further the absorption edge 14 shifts to higher-energy wavelengths and hence hypsochromically.

Figure 9:
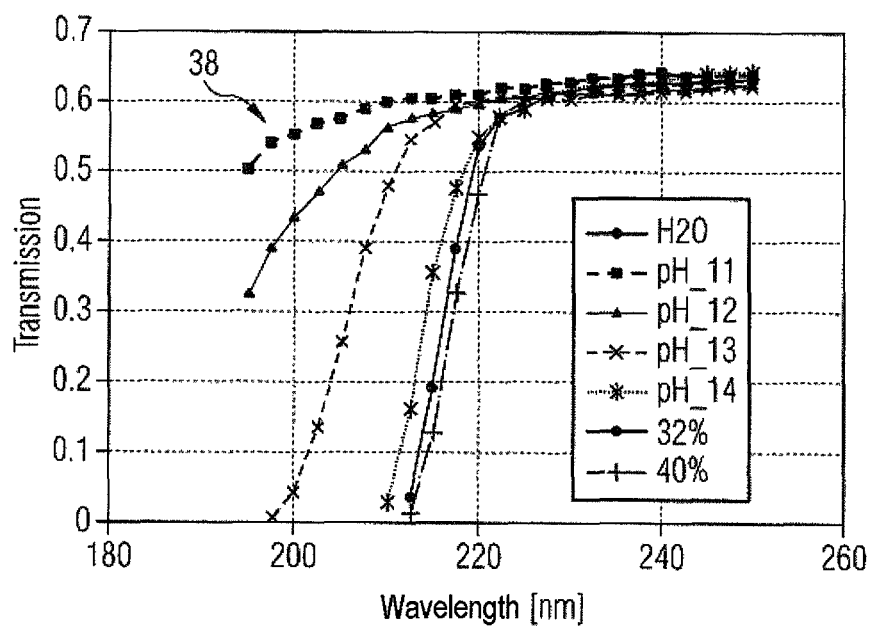
FIG. 9 shows a plurality of pH-dependent transmission spectra of H2O in the wavelength range between 180 nm and 260 nm.

FIG. 9 shows the transmission spectra 38 for pH values of 11 to 14. The different pH values of the water 11 were set by adding KOH; the optical layer thickness was 1 cm during the measurements. It is possible to identify that the absorption edge 14 in the transmission spectra 38 has a further bathochromic shift, even above pH=14, if additional KOH is added, as elucidated by the percent specifications 32% and 40%.

Figure 10A:
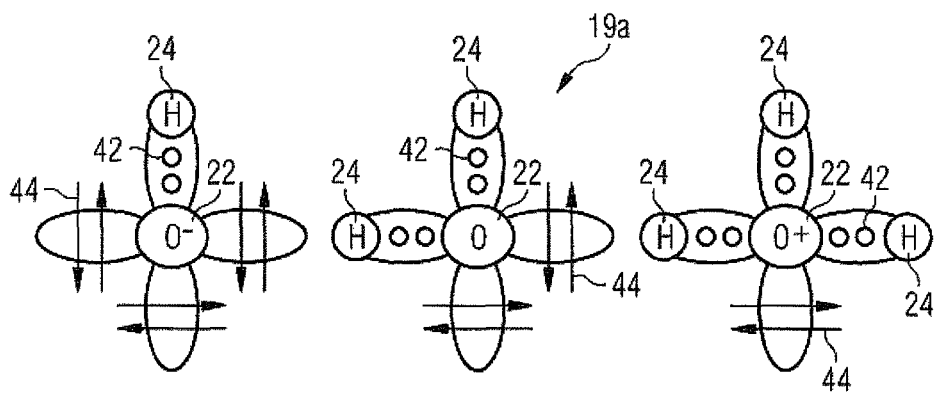
FIG. 10A shows a simplified planar representation of the atoms, the bonding and nonbonding electrons in the $OH^-$ molecule, in the $H_2O$ molecule and in the $H_3O^+$ molecule.

The bathochromic shift of the water absorption edge 14 with an increasing pH value could be explained as follows:

FIG. 10A illustrates, in simplified form, a planar representation of the OH$^-$, the H$_2$O and the H$_3$O$^+$ molecule, with bonding electrons 42 being illustrated as points and nonbonding electrons 44 being illustrated as arrows. This representation is also clarified by the structure representations in FIG. 10B. It is possible to identify that the OH$^-$ molecule has six nonbonding electrons 44 and two bonding electrons 42. The number of nonbonding electrons 44 reduces in the direction of the H$_3$O$^+$ molecule; they only total four in the H$_2$O molecule and only two in the H$_3$O$^+$ molecule, while the number of bonding electrons 42 increases, namely there are four in the H$_2$O molecule and six in the H$_3$O$^+$ molecule.

Figure 10B:
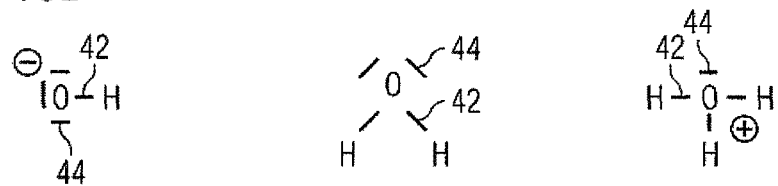
FIG. 10B shows a structural representation of the $OH^-$ molecule, the $H_2O$ molecule and the $H_3O^+$ molecule.
Figure 10C:
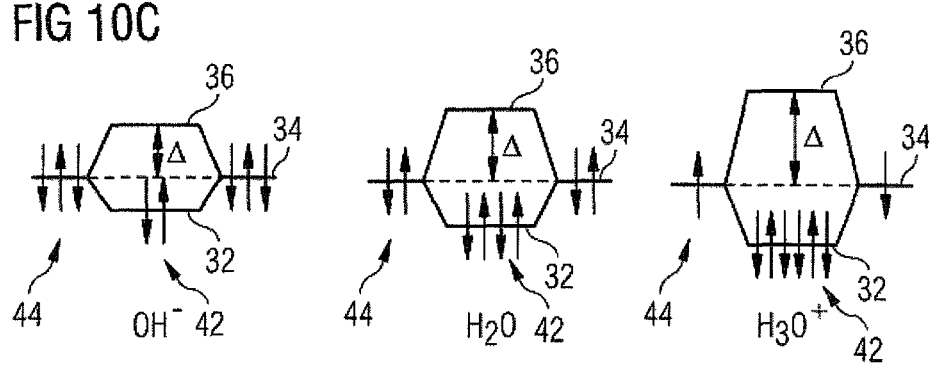
FIG. 10C shows a simplified representation of the electronic occupancy of the bonding, nonbonding and antibonding molecular orbitals from FIG. 4 for the $OH^-$ molecule, the $H_2O$ molecule and the $H_3O^+$ molecule.

The occupation of the nonbonding molecular orbitals 34 and bonding molecular orbitals 32 of the three molecules has once again been illustrated in FIG. 10C in simplified fashion. The unoccupied region in each case constitutes an antibonding molecular orbital 36.

As already described above, UV light 13$a$ excites electronic transitions 37 from nonbonding molecular orbitals 34 to antibonding molecular orbitals 36. The more nonbonding electrons 44 are available in the nonbonding molecular orbitals 34 for such an absorption transition, the greater the energetic split $\Delta$ becomes, i.e. the energetic spacing between the nonbonding molecular orbitals 34 and the antibonding molecular orbitals 36. The greater the split $\Delta$ is, the more energy is required to lift a nonbonding electron 44 into an unoccupied antibonding molecular orbital 36 as a result of excitation by light 13$a$. This means further that, in the case of the OH$^-$ molecule and hence in a region with a higher pH value, less energy is required to lift an electron into an unoccupied state. Hence, in this case, light 13$a$ with lower energy and hence with longer wavelengths is sufficient for the absorption, and so the absorption edge 14 shifts bathochromically.

In the sequence toward H$_3$O$^+$, the energetic split $\Delta$ between nonbonding molecular orbitals 34 and antibonding molecular orbitals 36 increases, and so ever higher energies are also required to enable an electronic transition 37. The result of this is that the absorption edge 14 shifts hypsochromically to higher light energies and hence to lower wavelengths.

Figure 11:
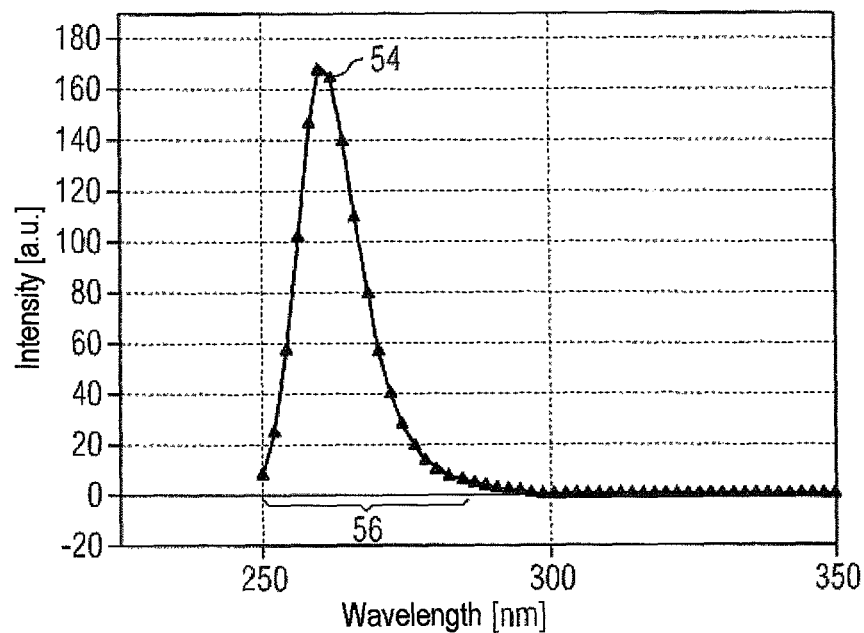
FIG. 11 shows a characteristic of an LED with an emission peak in the UV range about 265 nm.

FIGS. 11 through 14 show how the above-described observed effect can be realized in a sensor arrangement 46 for determining the pH value of a liquid 10. That is, FIG. 11 shows an intensity characteristic of an LED 48, which can be used as light source 50 for exciting liquid molecules 37$a$ in the liquid 10. The illustrated light source 50 has an emission peak 54 at approximately 265 nm and a spectral width 56 of approximately 50 nm.

Figure 12:
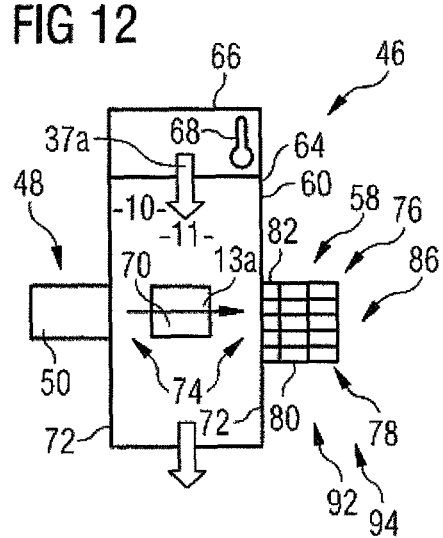
FIG. 12 shows a sensor arrangement for determining the pH value of a liquid.
Figure 13:
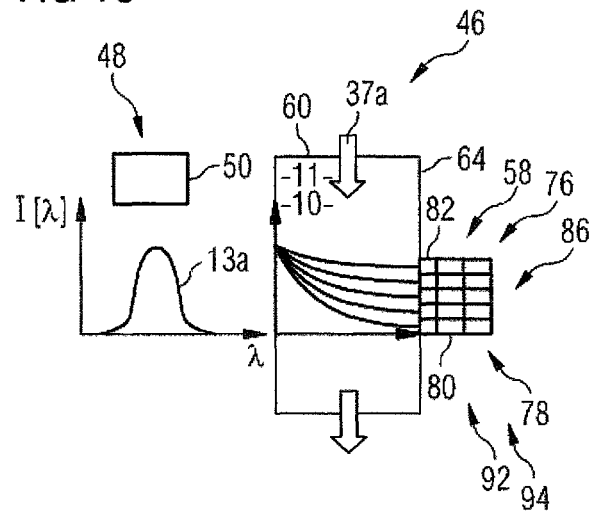
FIG. 13 shows a first embodiment of the sensor arrangement from FIG. 12 with illustrated excitation light.
Figure 14:
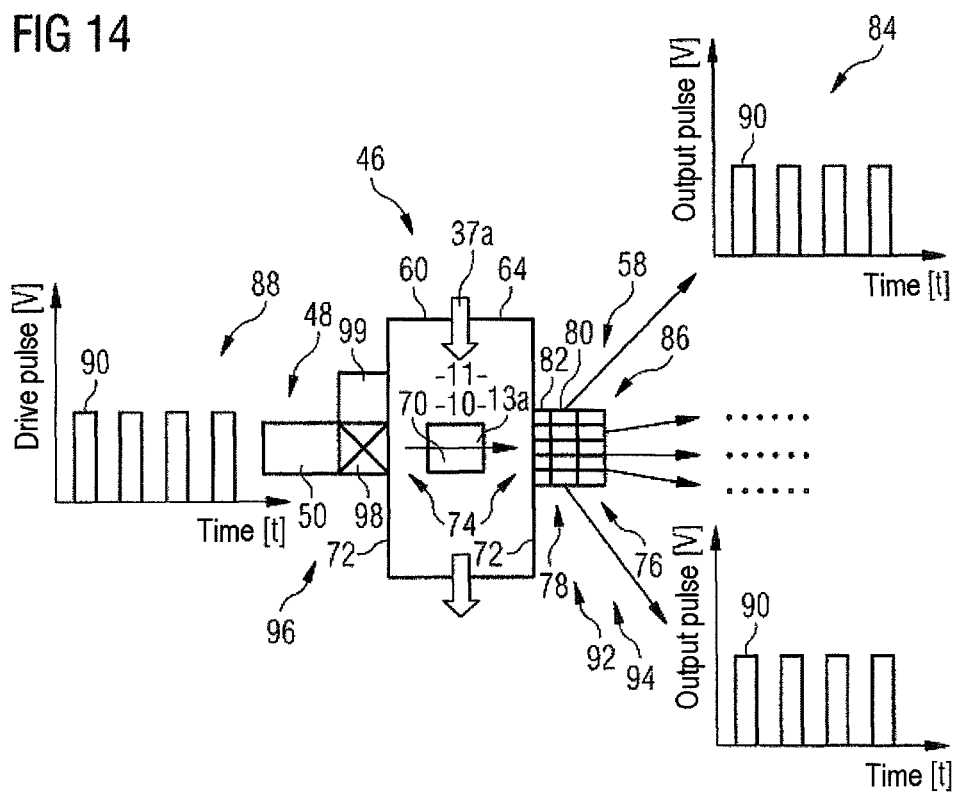
FIG. 14 shows a second embodiment of the sensor arrangement from FIG. 12 with illustrated excitation light.

This light source 50 can be used as excitation light source in a sensor arrangement 46 as shown in FIGS. 12 through 14. FIG. 12 shows the sensor arrangement 46 with the light source 50 and a detector apparatus 58, between which the liquid 10 to be measured, in this case water 11, is arranged in a carrier apparatus 60. In the present example, the carrier apparatus 60 is configured as conveying apparatus 64, which conveys the water 11 past the light source 50 and the detector apparatus 58 so that it is also possible to measure flowing water 11.

Upstream of the carrier apparatus 60 there is a temperature control apparatus 66 with a temperature measuring apparatus 68, where the temperature of the water 62 is set to a predetermined temperature and this temperature is checked by the temperature measuring apparatus 68. The conveying apparatus 64 is arranged in the beam path 70 of the light 13$a$ used for excitation. In order to enable the light 13$a$ to pass through the walls 72 of the conveying apparatus 64 in order thus to excite the liquid molecules 37$a$, the conveying apparatus 64 has an optically transparent region 74, which can, for example, be formed by sapphire windows or quartz windows, in the region of the beam path 70.

The detector apparatus 58 has a plurality of detectors 76, which together form a detector array 78. Each detector 76 is formed by a photodiode 80, which is optimized in terms of energy by means of a band-pass filter 82 such that it only detects light with a specific wavelength or a narrow wavelength range 13. This is because, as illustrated in FIG. 13, light 13$a$ with different wavelengths has different intensity profiles in the liquid 10, i.e. light 13$a$ of different wavelengths is absorbed to a different extent over the path which the light 13$a$ takes through the liquid 10. If the energetically optimized photodiodes 80 now capture different wavelength ranges 13, it is possible to create a characteristic intensity pattern 84 (FIG. 14) and the measurement can thus become even more precise. The intensity pattern 84 is created by a conversion apparatus 86 which is arranged downstream of the detector apparatus 58. The conversion apparatus 86 can include, for example, a microprocessor that is specifically programmed to create the intensity patterns discussed herein. The microprocessor can relate the produced absorption characteristic to a reference absorption characteristic associated with a specific pH value of the liquid as discussed herein.

In the first embodiment of the sensor arrangement 46, shown in FIG. 13, use is made of a light source 50 which continuously emits light 13$a$. An alternative embodiment is illustrated in FIG. 14. Here use is made of a pulsed light source 88, i.e. individual light pulses 90 are emitted at short time intervals. As can be seen in FIG. 14, the photodiodes 80 then likewise receive pulsed light 13$a$ with the same frequency, i.e. with the same time intervals at which the pulsed light source 88 emits the light pulses 90. If this is not the case, this indicates a malfunction in the whole sensor arrangement 46. This means that the use of the pulsed light source 88 automatically implements a self-testing apparatus 92 in the form of an overall monitoring apparatus 94. It is thus possible to determine quickly whether there is a fault at any point, i.e. at any electronic or optical part of the sensor arrangement 46.

Additionally, the embodiment of the sensor arrangement 46 shown in FIG. 14 has a light-source monitoring apparatus 96 as self-testing apparatus 92. Prior to contact of the light 13*a* used for excitation with the liquid 10 or with the optically transparent region 74 of the conveying apparatus 64, a beam splitter 98 is inserted into the beam path 70 of the light 13*a* used for excitation, which beam splitter diverts a component of the light 13*a* used for excitation perpendicularly onto a reference detector 99. As a result, this reference detector 99 can be used prior to contact with the liquid 10 to monitor the intensity of the light 13*a* emitted by the light source 50 and, as a result of a subsequent normalization of the absorption spectra 12 received by the photodiodes 80, it is possible to remove by calculation shifts which are caused by changes in the light intensity directly at the light source 50.

FIG. 15 shows how drinking water 100 is obtained by electrolyzing kerosene 102 in a fuel cell 104. Energy is obtained in the fuel cell 104 from the kerosene 102 or another suitable fuel 106, with water 11 accumulating as reaction product 108. After being conveyed out of the fuel cell 104, mineral substances 110 are added to the produced water 11. The sensor arrangement 46 is connected downstream of this chemical purification. Here the pH value of the water 11 is used to check whether there already is a sufficient amount of mineral substances 110 in the purified water 11 so as to be able to declare the water as drinking water 100. If this is not the case, the supply of mineral substances 110 can be increased by means of a regulating apparatus 112.

The electrochemical measurement of pH values is a conventional technology. The electrochemical measurement principle requires electrodes which have to be brought into contact with the liquid electrolyte to be measured. Contact corrosion and/or impurities can cause the signals measured by the sensor to drift, even though there has been no change in the pH value. Sensors known from the prior art therefore require regular recalibration in order to achieve reliable measurement results.

Measuring the pH value can be reduced to measuring an electric voltage by means of e.g. an ion-selective electrode (ISE), normally a glass electrode 200, or by using an ion-sensitive field effect transistor (ISFET) 201. What is common to all electrochemical pH measurement instruments is that they require regular recalibration in order to obtain reliable and reproducible measurements of the pH value. Such recalibration methods require reference solutions and trained staff in order to be able to be carried out. However, it is not possible to carry out recalibration methods if the pH value which is to be measured is situated in an unexpected measurement region of the routine measurement method.

The invention is based on the observation that the UV transparency of pure water 11 is reduced when chemicals which increase the pH value of the water 11 are added to the water 11. This observation renders it possible to construct optical pH sensors which do not require electrodes that are in contact with the liquid electrolyte. This is how two main advantages can be obtained: 1) All types of drift effects which originate from impurities and/or corrosion of the electrode can be eliminated; and 2) If the sensor is operated using A/C modulated UV light, it is possible to implement a self-testing apparatus 92, which is not available in currently utilized pH sensor designs. Such a sensor arrangement 46 can be used as follows.

Fuel cells 104 which are operated using kerosene 102 simultaneously produce electricity, deoxygenated air and water 11. In order to render this water 11 from the fuel cell 104 drinkable it needs to be mineralized. The proposed pH sensor arrangement 46 can be used to monitor this mineralization procedure. Compared to commercial designs, the sensor arrangement 46 has the following advantages. There is no need for buffer solutions or calibrations, installation-dependent it is possible for the sensor system or the sensor arrangement 46 to test itself, the upkeep of A/C light results in lower costs, and there is increased A/C usability.

The prior art has disclosed electrochemical measurement methods for measuring the pH value. Reliable measurements of the hydrogen-ion concentration in aqueous solutions are required for a number of reasons. In practice, the pH value, which is related to the $H^+$ concentration as stated below, is even more important than the $H^+$ concentration itself:

$$pH = -\log_{10}(H^+).$$

Measuring the pH value can be reduced to measuring an electric voltage by using e.g. an ion-selective electrode ISE, normally a glass electrode 200, or by using an ion-sensitive field effect transistor ISFET 201. Examples of a glass electrode-type 200 ion-selective electrode and of an ISFET 201 are illustrated in FIG. 16 (glass electrode 200) and FIG. 17 (ISFET 201). The pH value in aqueous solutions can be measured by both measurement arrangements.

What is common to both measurement principles is that the electrodes have to be immersed into the liquid medium in order to monitor the latter. What is common to all electrochemical pH measurement devices is that they require frequent regular recalibrations in order to obtain reliable and reproducible measurements of the pH value. Such recalibration methods require reference solutions and trained staff in order to be able to be carried out. However, it is not possible to carry out such recalibration methods if the pH value which is to be measured is situated in an unexpected region of a routine measurement method.

In order to be able to solve these problems in a practical fashion, a novel way is described for measuring the pH value, without using electrochemistry and deteriorating electrodes. As described below, this novel method is based on the observation that liquid water 11 has a pH-dependent absorption in the UV range.

The optical absorption of water 11 is already known. FIG. 1 shows the optical absorption spectrum 12 of water 11 over a large wavelength range 13. Water 11 is almost completely transparent in the visible range of the spectrum. Minimal absorption occurs in the range of visible (VIS) blue light. At this wavelength, the penetration depth of the light 13*a* in pure water 11 is of the order of $10^4$ cm to 100 m. At shorter and longer wavelengths the optical absorption increases by a number of orders of magnitude. In the case of far infrared light (FIR; $\lambda > 10$ μm), the optical absorption is dominated by molecular rotations of the water molecules 19*a*. In the range of mid and near infrared light (MIR and NIR) of the spectrum, the optical absorption is dominated by molecular vibrations 19, as shown in FIGS. 2A through 2F. A prominent absorption peak 18 occurs around 3700 $cm^{-1}$, corresponding to a wavelength of approximately 3 μm. At this wavelength, the optical penetration depth is only of the order of 1 μm. This pronounced MIR absorption is due to the excitation of symmetric and asymmetric vibrations 19 of the O—H bond, as shown in FIGS. 2A and 2B. Harmonic absorptions of these vibrations 19 occur at following shorter NIR wavelengths and extend far into the visible range of the optical spectrum. The result of the symmetric and asymmetric stretching, libration and bending vibrations of the $H_2O$ molecule, as shown in FIGS. 2A through 2F, is optical absorptions at wavelengths that are greater than approximately 400 nm, as illustrated in FIG. 3.

The part of the optical spectrum of water 11, illustrated in FIG. 1, which is most relevant to measuring the pH value is the short-wavelength branch which starts in the visible blue range of the spectrum and extends into the range of the far ultraviolet (FUV) light. It emerges from FIG. 1 that the optical absorption increases by eight orders of magnitude when the wavelength decreases from 200 nm to 100 nm. This pronounced absorption is due to electronic transitions 37 in the liquid water 11. The electronic structure of the $H_2O$ molecule and the corresponding molecular orbitals 32, 34, 36 are shown in FIGS. 4 and 5. That is, FIG. 4 shows the electronic structure of an $H_2O$ molecule. On the left-hand side FIG. 4 shows an oxygen atomic orbital 26 and on the right-hand side it shows two hydrogen atomic orbitals 24, with the energy of the orbitals increasing toward the top. Illustrated in the center is the electronic arrangement of the water molecular orbitals 32, 34, 36. Transitions between occupied nonbonding molecular orbitals 34 and unoccupied antibonding molecular orbitals 36 result in the optical absorption in the UV wavelength range 13.

FIG. 5 shows the spatial arrangement of the valence molecular orbitals of an $H_2O$ molecule with two doubly occupied nonbonding oxygen orbitals. Points represent unshared electron pairs in an $sp^3$ hybrid orbital of an oxygen, the unfilled orbitals represent O—H s-bonds between an oxygen $sp^3$ hybrid orbital and an H 1s orbital.

Optical transitions are possible between occupied and empty molecular states. Proceeding from the state $1b_1$, transitions are therefore possible into the states $3a_1$ or $2b_2$. These transitions connect doubly occupied, nonbonding oxygen atom states with antibonding OH molecule states. It is known that the electronic occupation of nonbonding states destabilizes the covalent chemical bond, cf., for example, M. Stutzmann, Phil. Mag. B, volume 56, 63-70, 1987. Found to be in agreement with this is the observation that UV photons with a wavelength of approximately 125 nm photochemically dissociate $H_2O$ molecules 28 to OH and H radicals according to the following equation:

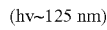

(hv~125 nm)

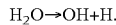

$H_2O \rightarrow OH+H$.

The invention is based on the fundamental observation that the optical absorption of water 11 is pH-dependent. In respect of measuring the pH value, it was a fundamental observation that the optical UV absorption of water 11 is pH-dependent. This observation was made by the applicant during experiments in respect of semiconductor etching.

FIG. 9 shows the optical transmission of UV light through water 11 in the case of a layer thickness of 1 cm, with a series of pH values being set by addition of increasing amounts of KOH. The data from FIG. 9 can be converted to optical absorption values using the following equation:

$T=(1-R) \times \exp(-\alpha \times d)$, where T is the optical transmission, R is the reflection coefficient, d is the thickness of the cuvette and a is the optical absorption.

Figure 8:
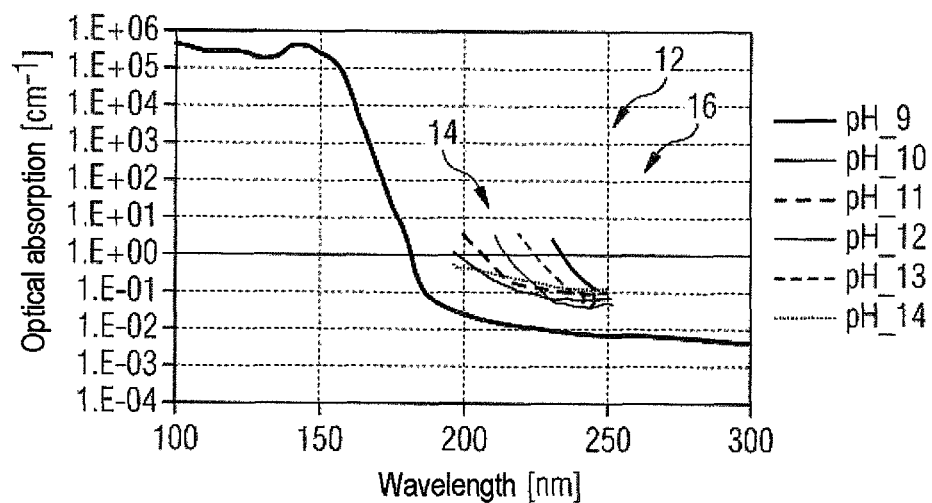
FIG. 8 shows a detailed section between 100 nm and 300 nm from FIG. 7.

The data measured in FIG. 9 can then be compared to the spectrum 40, from the literature, shown in FIG. 1; by way of example, this is illustrated in FIG. 7. FIGS. 7 and 8 illustrate the optical absorption spectrum of water 11. Here, the thick line is the spectrum 40 from the literature. The other lines represent pH-dependent measurements. FIG. 7 is an overview spectrum and FIG. 8 is a partial spectrum in the ultraviolet range. This means that FIG. 7 shows an overview spectrum similar to FIG. 1, with FIG. 8 showing the UV range in more detail. The measurements were only carried out in a small part of the UV absorption edge 14 of the water 11 since a cuvette with an optical path length of 1 cm was used. If larger regions of the optical absorption edge 14 are to be measured it is necessary to use shorter or much longer optical path lengths.

FIG. 6 shows spectra 40, from the literature, of the optical absorption spectrum 12 of water 11, with the literature values being scattered in the UV range. The different positioning of the absorption edge 14 could be the result of slightly different pH values of the measured water 11 having been present.

FIG. 6 therefore shows data from different published sources, with it being possible to see that the data is not quite in agreement with respect to the precise position of the UV absorption edge 14. If one considers this observation in light of the observations on which the invention is based, this difference could be based on the fact that the measurements have been carried out without the scientists being aware of the pH-dependence of the optical absorption spectrum 12 and therefore inadvertently having used water samples that had slightly different pH values.

FIGS. 10A through 10C summarizes a possible explanation of the pH effect during optical absorption. FIG. 10A shows the three possible charge states of water molecules within liquid water 11. FIG. 10C shows the electronic occupation of nonbonding and antibonding states in the three charge states of water 11. Bonding electrons are illustrated by points and nonbonding electrons are illustrated by arrows. FIG. 10A shows a simplified 2D version of the valence molecular orbitals of a neutral water molecule 19a (center) and the two ionized states thereof (left and right). FIG. 10C shows the electronic occupancy of the bonding 32 and nonbonding 34 molecular orbitals of the three different ionic states. FIG. 10C shows that the occupation of the nonbonding molecular orbitals 34 reduces according to the sequence $OH^-$, $H_2O$, $H_3O^+$. In $OH^-$ ions, more electrons are available for an optical transition into OH-antibonding molecular orbitals 36 than in the neutral and positively charged state. This different availability of electrons that can be excited has an effect on the strength of the optical absorption. It is very probable that a stronger absorption effect is based on different degrees of negative charge being available at the central oxygen ion: excessive negative charge destabilizes the covalent bond and results in a reduced split $\Delta$ of the nonbonding molecular orbitals 34 and antibonding molecular orbitals 36 in the $OH^-$ ion state. This reduction in the split $\Delta$ qualitatively causes the shift of the optical absorption edge 14 to lower energies, i.e. bathochromic. If one follows the sequence from $H_2O$ to $H_3O^+$, the central oxygen atom becomes ever more positive. The increased effective nuclear charge at the oxygen atom should in this case lead to stronger OH bonds and therefore result in a larger split $\Delta$ between nonbonding molecular orbitals 34 and antibonding molecular orbitals 36. The UV absorption edge 14 should therefore migrate to higher photon energies if the pH value is reduced to below pH=7. This explanation qualitatively corresponds to the observations shown in FIG. 7 through 9.

In possible practical sensor applications, the high-energy position of the UV absorption edge 14 has natural boundaries in the region of 6-7 eV. This is because in this range of the photon energies there are only a limited number of optically transparent and mechanically stable window materials, such as e.g. sapphire and quartz. In this context it is advantageous if use is made of additional methods in order to capture the pH value optically by virtue of using lower photon energies. Such options exist in the region of 1000 nm photon energy, where the optical absorption is dominated by harmonics of the OH stretching vibration. The precise spectral position of the OH stretching vibration likewise depends on the strength of the absorbing OH bond. It is for this reason that the strength of the absorbing OH bond depends on the charge state of the central oxygen atom and hence also on the pH value of the liquid electrolyte.

The invention is therefore based on the fundamental concept that the pH value can be monitored optically. The observation of a pH-dependent optical absorption can be used in the field of sensor technology. As a result, the pH value of an aqueous solution can be determined by optical devices only, i.e. without electrodes being immersed in the liquid electrolyte.

A possible realization of an optical measurement of the pH value is illustrated in FIG. 12, where a water-filled optical absorption cell with a light source 50 in the form of a UV-LED 48 and a photodetector array 78 are illustrated, with each detector 76 having a different spectral response characteristic. UV light 13a from a light source 50 with a relatively broad emission spectrum is transmitted through the liquid 10 which is to be measured, and detected after passage through the liquid volume. In order to obtain a defined irradiation, use is made, for example, of a UV-LED 48 which has the radiation characteristic illustrated in FIG. 11, with a peak emission at a wavelength of approximately 265 nm and with a spectral width of approximately 50 nm.

The detector apparatus 58 is constructed such that it has an array of photodiodes 80 equipped with narrow band-pass filters 82, with each band-pass filter 82 having a different central wavelength. The photodetectors themselves can be e.g. silicon photodiodes 80 or detectors which are formed from more broad-band materials than silicon, for example from SiC, GaN or ZnO.

FIG. 13 shows the spectral characteristic of the UV emission source and the wavelength-dependent optical absorption characteristic 16 (FIG. 1) within the liquid 10. Each spectral component is attenuated at a different rate during the passage of the UV light 13a through the liquid 10. The silicon detectors 76 are spectrally filtered since the light penetration depth depends on the color of the light 13a. It is thereby possible to produce an intensity distribution at the individual detectors 76 which is dependent on the pH value. The spectrally filtered sensor array therefore produces an intensity pattern 84 which is dependent on the exact position of the UV absorption edge 14 and hence on the pH value of the liquid 10.

Determining the pH value optically is advantageous in that there is no need to immerse electrodes into liquids 10 which may be aggressive or corrosive. The drift of values as a result of changes on the electrode or as a result of corrosion is therefore not expected in the present sensor arrangement 46.

Furthermore, an optical pH sensor is advantageous in that it is possible to integrate a self-testing apparatus 92. FIG. 14 shows the basic design of an optical sensor system with an implemented self-testing apparatus 92.

An A/C modulated light source 50 with a known frequency is used as UV light source 50. If all components of the pH sensor arrangement 46 are functioning correctly, this known frequency can be observed in every single photodetector output signal. This means that if this frequency is observed, this is proof that the whole chain of electrical and optical components of the sensor arrangement 46 is operating correctly. As can be seen in FIG. 14, all spectrally filtered SI detectors 76 show an output pulse at the same position on a time axis, corresponding to the frequency of the drive pulse from the light source 50. Deterioration of the UV light source 50 can be captured, and hence corrected, by virtue of arranging a beam splitter 98 and a broad-band reference detector 99 on the emission side of the carrier apparatus 60, e.g. a cuvette.

The sensor arrangement 46 renders it possible to capture changes in the pH value of aqueous solutions by observing shifts in the UV absorption edge 14. To this end, various technical devices can be used for capturing this shift, for example the arrangement of color-dependent sensors like in the shown detector array 78, or else the use of produced diffraction patterns. Furthermore, it is possible to use a sensor arrangement 46 which detects changes in the spectral position of OH vibration peaks which are connected to a change in the pH value of the liquid 10. To this end, use can be made of various technical devices which operate in the lower-energy absorption range, for example, in the visible, near IR or mid IR range.

Additionally, it is possible to implement a self-testing apparatus 92, as shown in FIG. 14, in the sensor arrangement 46. To this end, the technical devices illustrated in FIG. 14 in an exemplary fashion can be used for such self-tests.

GENERAL INTERPRETATION OF TERMS

In understanding the scope of the present invention, the term "comprising" and its derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms, "including," "having" and their derivatives. Also, the terms "part," "section," "portion," "member" or "element" when used in the singular can have the dual meaning of a single part or a plurality of parts. The term "detect" as used herein to describe an operation or function carried out by a component, a section, a device or the like includes a component, a section, a device or the like that does not require physical detection, but rather includes determining, measuring, modeling, predicting or computing or the like to carry out the operation or function. The term "configured" as used herein to describe a component, section or part of a device includes hardware and/or software that is constructed and/or programmed to carry out the desired function.

While only selected embodiments have been chosen to illustrate the present invention, it will be apparent to those skilled in the art from this disclosure that various changes and modifications can be made herein without departing from the scope of the invention as defined in the appended claims. For example, the size, shape, location or orientation of the various components can be changed as needed and/or desired. Components that are shown directly connected or contacting each other can have intermediate structures disposed between them. The functions of one element can be performed by two, and vice versa. The structures and functions of one embodiment can be adopted in another embodiment. It is not necessary for all advantages to be present in a particular embodiment at the same time. Every feature which is unique from the prior art, alone or in combination with other features, also should be considered a separate description of further inventions by the applicant, including the structural and/or functional concepts embodied by such feature(s). Thus, the foregoing descriptions of the embodiments according to the present invention are provided for illustration only, and not for the purpose of limiting the invention as defined by the appended claims and their equivalents.

What is claimed is:
1. A method for determining the pH value of a liquid comprising:
exciting liquid molecules in the liquid using light with a predetermined wavelength;

capturing by a detector apparatus an intensity component, transmitted by the liquid in a predetermined wavelength range, of the light used for excitation;

producing by the detector apparatus at least one of a wavelength absorption characteristic and an intensity absorption characteristic from the captured intensity component; and relating the produced absorption characteristic produced by the detector apparatus to a reference absorption characteristic associated with a specific pH value of the liquid to determine the specific pH value of the liquid.

2. The method as claimed in claim 1, wherein
at least one of an absorption spectrum and a diffraction pattern is produced as absorption characteristic.

3. The method as claimed in claim 2, wherein
at least one of electronic transitions and vibrations are excited in the liquid molecules.

4. The method as claimed in claim 2, wherein
the liquid molecules are excited by at least one of the following: ultraviolet light in a wavelength range from 100 nm to 330 nm; light in a wavelength range of visible light, light in a wavelength range of mid infrared light, and light in a wavelength range of near infrared light in the wavelength range from 800 nm to 1200 nm.

5. The method as claimed in claim 1, wherein
at least one of electronic transitions and vibrations are excited in the liquid molecules.

6. The method as claimed in claim 1, wherein
the liquid molecules are excited by at least one of the following: ultraviolet light in a wavelength range from 100 nm to 330 nm; light in a wavelength range of visible light, light in a wavelength range of mid infrared light, and light in a wavelength range of near infrared light in the wavelength range from 800 nm to 1200 nm.

7. The method as claimed in claim 1, wherein
a plurality of intensity components of the light used for excitation are captured separately from one another in different predetermined wavelength ranges with an intensity pattern being produced as at least one of the wavelength absorption characteristic and the intensity absorption characteristic from the plurality of separately captured intensity components.

8. The method as claimed in claim 1, wherein
the liquid molecules are excited by pulsed A/C modulated light with at least one of a frequency of the intensity component of the pulsed light transmitted through the liquid being captured separately from one another in a plurality of different predetermined wavelength ranges and the intensity component of the light used for excitation, which is emitted by the light source, is captured prior to entry into the liquid.

9. A method for monitoring a pH value of a liquid, comprising:
repeatedly creating, at predetermined time intervals or continuously, an absorption characteristic of the liquid by performing the method as claimed in claim 1 with samples being taken from the liquid or the liquid being continuously conveyed past at least one of a light source and a detector apparatus; and capturing the spectral shift of the absorption characteristic.

10. A method for obtaining drinking water from a fuel for aircraft, comprising:
electrolyzing the fuel in a fuel cell to form water and further reaction products;
adding mineral substances to the water; and
performing the method for monitoring the pH value as claimed in claim 9.

11. A sensor arrangement for determining a pH value of a liquid comprising:
a light source configured to irradiate the liquid with light that excites liquid molecules of the liquid;
a carrier apparatus configured to position the liquid in a beam path of the light used for excitation;
a detector apparatus configured to capture an intensity component transmitted through the liquid of the light used for excitation; and
a conversion apparatus configured to produce at least one of a wavelength absorption characteristic and an intensity absorption characteristic from the captured intensity component, and to relate the produced absorption characteristic to a reference absorption characteristic associated with a specific pH value of the liquid to determine the specific pH value of the liquid.

12. The sensor arrangement as claimed in claim 11, wherein
the light source includes an LED, and at least one of the following:
the emitted light has an emission peak in a wavelength range from 255 nm to 270 nm and a spectral width of 40 nm to 60 nm; and
the light source is configured to emit A/C modulated pulsed light.

13. The sensor arrangement as claimed in claim 11, wherein the carrier apparatus includes at least one of the following
a conveying apparatus configured to convey the liquid past at least one of the light source and the detector apparatus; and
a region which is optically transparent to the light used for excitation, with the region being formed by sapphire or quartz windows.

14. The sensor arrangement as claimed in claim 13, further comprising at least one of the following
a temperature control apparatus configured to control the temperature of the liquid; and
a temperature measuring apparatus configured to measure the temperature of the liquid prior to irradiating the liquid by the light source.

15. The sensor arrangement as claimed in claim 11, wherein the detector apparatus includes at least one detector formed by a photodiode including Si, SiC, GaN or ZnO.

16. The sensor arrangement as claimed in claim 11, wherein
the detector apparatus includes a detector array which comprises a plurality of detectors configured for separate capture of the intensity component of the light used for excitation in a plurality of different wavelength ranges, the detectors being configured by photodiodes with band-pass filters set to different wavelengths.

17. The sensor arrangement as claimed in claim 11, further comprising
a self-testing apparatus configured to test the sensor arrangement, the self-testing apparatus comprising at least one of an overall monitoring apparatus configured to monitor all electronic and optical parts of the sensor arrangement and a light-source monitoring apparatus configured to monitor the light intensity emitted by the light source.

18. The sensor arrangement as claimed in claim 17, wherein
the overall monitoring apparatus includes a pulsed light source configured to emit light which excites the liquid molecules, and a plurality of detectors configured to capture separately from one another the pulse frequency of the light used for excitation in a plurality of different wavelength ranges.

19. The sensor arrangement as claimed in claim 18, wherein the light-source monitoring apparatus includes a beam splitter, arranged prior to the entry into the liquid in the beam path of the light used for excitation, to divert a component of the light used for excitation, and a broadband reference detector configured to capture the intensity of the diverted light.

20. The sensor arrangement as claimed in claim 17, wherein the light-source monitoring apparatus includes a beam splitter, arranged prior to the entry into the liquid in the beam path of the light used for excitation, to divert a component of the light used for excitation, and a broadband reference detector configured to capture the intensity of the diverted light.

\* \* \* \* \*